United States Patent
Stridiron et al.

(10) Patent No.: US 7,575,395 B2
(45) Date of Patent: Aug. 18, 2009

(54) SYSTEM FOR MEASURING MATERIAL PROPERTIES FROM A MOVING CONSTRUCTION VEHICLE

(75) Inventors: Laura Stridiron, Cornelius, NC (US); Michael James Scotese, Carlisle, PA (US)

(73) Assignee: Volvo Construction Equipment AB, Eskilstuna (SE)

( * ) Notice: Subject to any disclaimer, the term of this patent is extended or adjusted under 35 U.S.C. 154(b) by 316 days.

(21) Appl. No.: 11/789,950

(22) Filed: Apr. 26, 2007

(65) Prior Publication Data

US 2007/0201951 A1 Aug. 30, 2007

Related U.S. Application Data

(63) Continuation of application No. 10/490,133, filed as application No. PCT/US02/29882 on Sep. 19, 2002, now Pat. No. 7,226,239.

(60) Provisional application No. 60/323,787, filed on Sep. 19, 2001.

(51) Int. Cl.
E01C 23/01 (2006.01)
(52) U.S. Cl. .................................. 404/84.1; 404/84.05
(58) Field of Classification Search ............ 404/84.05, 404/84.1, 101, 128
See application file for complete search history.

(56) References Cited

U.S. PATENT DOCUMENTS

| 3,964,834 | A | 6/1976 | Paramythioti et al. |
| 4,149,253 | A | 4/1979 | Paar et al. |
| 4,979,197 | A | 12/1990 | Troxler et al. |
| 5,452,966 | A | 9/1995 | Swisher, Jr. |
| 5,588,776 | A | 12/1996 | Swisher et al. |
| 5,619,193 | A | 4/1997 | Doherty et al. |
| 5,745,051 | A | 4/1998 | Doherty et al. |
| 5,900,736 | A | 5/1999 | Sovik et al. |
| 5,952,561 | A | 9/1999 | Jaselskis et al. |
| 6,122,601 | A | 9/2000 | Swanson et al. |
| 6,414,497 | B1 | 7/2002 | Sovik et al. |
| 6,460,006 | B1 | 10/2002 | Corcoran |
| 6,803,771 | B2 | 10/2004 | Sovik et al. |
| 6,827,524 | B2 | 12/2004 | Starry et al. |
| 6,973,821 | B2 | 12/2005 | Corcoran |
| 7,226,239 | B2 * | 6/2007 | Stridiron et al. ............ 404/84.1 |

FOREIGN PATENT DOCUMENTS

DE   297 23 171 U1   4/1998
EP   0246937   11/1987

* cited by examiner

*Primary Examiner*—Gary S Hartmann
(74) *Attorney, Agent, or Firm*—Michael Best & Friedrich LLP (57) ABSTRACT

A system is for sensing a property of a material mat from a construction vehicle. The system includes a sensor for sensing the material property and a positioning mechanism connected with the vehicle and with the sensor. The mechanism displaces the sensor between first and second positions with respect to the vehicle as the vehicle displaces with respect to the material mat. The first sensor position is spaced a substantial distance above the mat upper surface. The second sensor position is located proximal to or on the mat surface such that the sensor is able to sense the material property in the second position. A controller operates the mechanism to sequentially displace the sensor from the first to second positions, permit the sensor to remain disposed at the second position for a period of time, and displace the sensor from the second to first positions after the period of time.

8 Claims, 7 Drawing Sheets

SYSTEM FOR MEASURING MATERIAL PROPERTIES FROM A MOVING CONSTRUCTION VEHICLE

RELATED APPLICATIONS

This application is a continuation of U.S. application Ser. No. 10/490,133, filed Aug. 13, 2004, now U.S. Pat. No. 7,226,239 which was the National Stage of International Application No. PCT/US02/29882, filed Sep. 19, 2002, which claims the benefit of U.S. Provisional application No. 60/323,787, filed Sep. 19, 2001, entitled "System for Measuring Properties from a Moving Construction Vehicle", which is incorporated herein by reference.

BACKGROUND OF THE INVENTION

The present invention relates to construction vehicles, and more particularly to systems for measuring material properties used with construction vehicles.

Certain construction vehicles, such as pavers and compactors, are used to form mats of asphalt, concrete or similar materials for such applications as roadways, airport runways, parking lots, etc. The finished material mats are typically required to have certain properties (e.g., density) that have a measured value within a specified range, such as for the purpose of meeting state highway regulations. Often, it is necessary for vehicle operators to measure these material properties during the construction process, for example during compaction operations, in order to gauge their progress toward meeting these material requirements.

With presently known systems for measuring certain material properties, it is typically necessary to hold the sensor device(s) stationary upon or proximal to a portion of the material mat being evaluated. In most cases, the sensor is an independent unit or is mounted on its own frame or carrier, but certain sensing systems are mounted on a construction vehicle. When using such vehicle-mounted sensing systems, the vehicle must typically be stopped at a particular location on the mat for a period of time necessary to take accurate measurements of the material properties. Therefore, the construction process being performed by the vehicle, such as a compaction operation, must be interrupted for this period of time.

In view of the limitations of presently know sensing systems as discussed above, it would be desirable to have a sensing system for construction vehicles that can operate without the need to interrupt the construction process.

SUMMARY OF THE INVENTION

In one aspect, the present invention is a device for deploying a sensor from a moving construction vehicle, the sensor being used to sense a property of a material mat having an upper surface. The deployment device comprises a positioning mechanism connected with the vehicle and connectable with the sensor. The mechanism is configured to displace the sensor between first and second vertical positions with respect to the material mat as the vehicle displaces with respect to the mat. The first sensor position is spaced a substantial distance above the mat upper surface. The second sensor position is located one of proximal to the mat surface and on the mat surface, the sensor being able to sense the material property when disposed in the second position.

In another aspect, the present invention is a system for sensing a property of a material mat from a construction vehicle, the material mat having an upper surface. The sensing system comprises a sensor configured to sense the material property and a positioning mechanism connected with the vehicle and connected with the sensor. The mechanism is configured to displace the sensor between a first position spaced a substantial distance above the mat upper surface and a second position located one of proximal to the mat surface and on the mat surface. Further, a controller is configured to operate the positioning mechanism such that the mechanism sequentially displaces the sensor from the first position to the second position, permits the sensor to remain generally disposed at the second position for a period of time, and displaces the sensor from the second position to the first position after the period of time.

In a further aspect, the present invention is also a device for deploying a material sensor from a construction vehicle, the sensor being used to sense a property of a material mat having an upper surface. The deployment device comprises a positioning mechanism connected with the vehicle and connected with the sensor. The mechanism is configured to displace the sensor between a first position spaced a substantial distance above the mat upper surface and a second position located one of proximal to the material mat and on the material mat. A controller is configured to operate the positioning mechanism such that the mechanism sequentially displaces the sensor from the first position to the second position, permits the sensor to remain generally disposed at the second position for a period of time, and displaces the sensor from the second position to the first position after lapse of the period of time.

In yet another aspect, the present invention is also a system for sensing a property of a material mat during travel of a construction vehicle, the mat having an upper surface. The sensing system comprises a sensor configured to sense a property of the material mat. A positioning mechanism is connected with the vehicle and with the sensor and is configured to displace the sensor between first and second positions with respect to the vehicle as the vehicle displaces with respect to the material mat. The first sensor position is spaced a substantial distance above the mat upper surface. The second sensor position is located either proximal to the material mat or on the material mat, the sensor being able to sense the material property when disposed in the second position.

In yet a further aspect, the present invention is also a further aspect, the present invention is also a device for deploying a material sensor from a construction vehicle, the sensor being used to sense a property of a material mat having an upper surface. The deployment device comprises a flexible connective member having a first end connected with the sensor and an opposing second end. A rotary actuator is connected with the vehicle and has a rotatable shaft. The connective member second end is connected with the actuator shaft such that rotation of the shaft displaces the sensor between first position spaced a substantial distance above the mat upper surface and a second position located one of proximal to the material mat and on the material mat. Further, a logic circuit is configured to operate the actuator such that the sensor is sequentially displaced from the first position to the second position, permitted to remain generally disposed at the second position for a period of time, and displaced from the second position to the first position after lapse of the period of time.

BRIEF DESCRIPTION OF THE DRAWINGS

The foregoing summary, as well as the detailed description of the preferred embodiments of the present invention, will be better understood when read in conjunction with the appended drawings. For the purpose of illustrating the invention, there is shown in the drawings, which are diagrammatic, embodiments that are presently preferred. It should be understood, however, that the present invention is not limited to the precise arrangements and instrumentalities shown. In the drawings:

FIGS. 1A-1D, collectively FIG. 1, are side elevational views of a construction vehicle having a sensing system in accordance with the present invention, each view depicting a different position of a preferred structure of a positioning mechanism during a sensing operation;

FIGS. 6A-6D, collectively FIG. 6, are more diagrammatic side elevational views of the construction vehicle having the sensing system of the present invention, each view depicting a different position of an alternative structure of a positioning mechanism during a measuring operation.

DETAILED DESCRIPTION OF THE PREFERRED EMBODIMENTS

Certain terminology is used in the following description for convenience only and is not limiting. The words "right", left", "lower", "upper", "upward", "down" and "downward" designate directions in the drawings to which reference is made. The words "front", "frontward" and "rear", "rearward" refer to directions toward and away from, respectively, a designated front end of a construction vehicle. The terminology includes the words specifically mentioned above, derivatives thereof, and words or similar import.

Referring now to the drawings in detail, wherein like numbers are used to indicate like elements throughout there is shown in FIGS. 1-7 a presently preferred embodiment of a system 10 for sensing a property of a mat of material M from a construction vehicle 1, the mat M having an upper surface S. The sensing system 10 basically includes a sensor 12 configured to measure a property of the material mat M and a deployment device 11 for deploying the sensor 12 from the vehicle 1. The deployment device 11 comprises a positioning mechanism 14 connected with the vehicle 1 and connected (or connectable) with the sensor 12. The mechanism 14 is configured to displace the sensor device 12 between first and second vertical positions $P_1$, $P_2$ with respect to the material mat M as the vehicle 1 travels or displaces with respect to the mat M. The first sensor position $P_1$ is spaced a substantial distance $d_s$ above the mat upper surface S, the sensor 12 being preferably located proximal to the vehicle chassis 2 when disposed in the first position $P_1$. The second sensor position $P_2$ is spaced from the chassis 2 and is located either proximal to the mat surface S or disposed on the mat surface S, the sensor 12 being able to sense the material property when disposed in the second position $P_2$.

Preferably, the deployment device 11 further comprises a logic circuit 40 configured to operate the positioning mechanism 14 such that the mechanism 14 sequentially displaces the sensor 12 from the first position $P_1$ to the second position $P_2$, permits the sensor 12 to remain generally disposed at the second position $P_2$ for a period of time, and displaces the sensor 12 from the second position $P_2$ to the first position $P_1$ after lapse of the period of time. Thus, the deployment device 11 enables the sensing system 10 to measure one or more properties of the material mat M, preferably at least material density, as the vehicle 1 linearly displaces or "travels" upon or adjacent to the material mat M. Each of the above-discussed basic elements of the sensing system 10 is described in further detail below.

Referring particularly to FIG. 1, the sensing system 10 is preferably used with a compacting vehicle 1, most preferably with a double-drum compactor 1 having a chassis 2 and front and rear drums 3A, 3B, respectively, rotatably attached to the chassis 2. With this preferred application, the material mat M is preferably a mat formed of paving material, such as asphalt, concrete, "superpave", "quickrete", or any other appropriate paving material. Alternatively, the compacting vehicle 1 may be a soil compacting vehicle (not shown), which typically include only a single compacting drum, such that the material mat M is formed of soil or landfill material. Further, although the sensing system 10 is preferably used with a compacting vehicle 1, the system 10 may alternatively be used with any other type of construction vehicle 1, such as a paver, a material transfer vehicle (an "MTV") or any other vehicle used in the construction of a mat of material M (none depicted).

Figure 5:
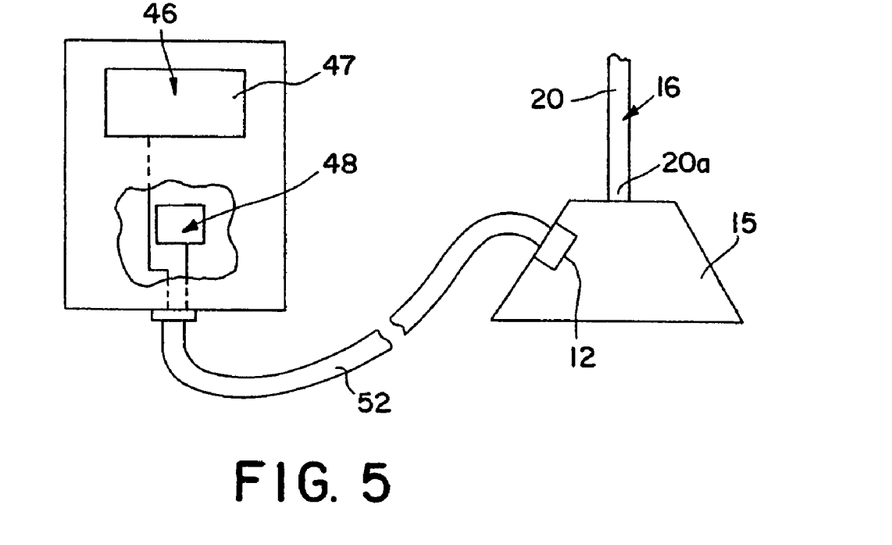
FIG. 5 is a diagrammatic view of preferred sensor device.
Figure 6A:
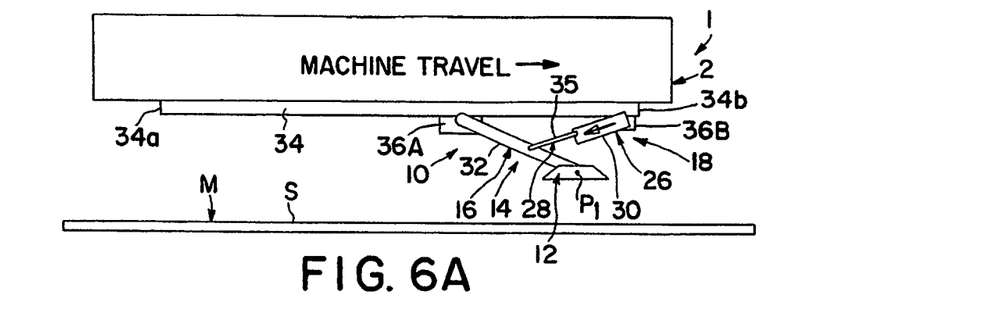
Figure 6B:
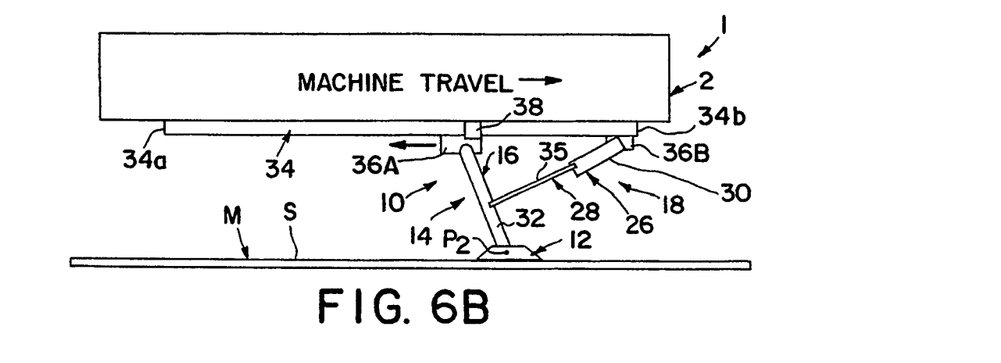
Figure 6C:
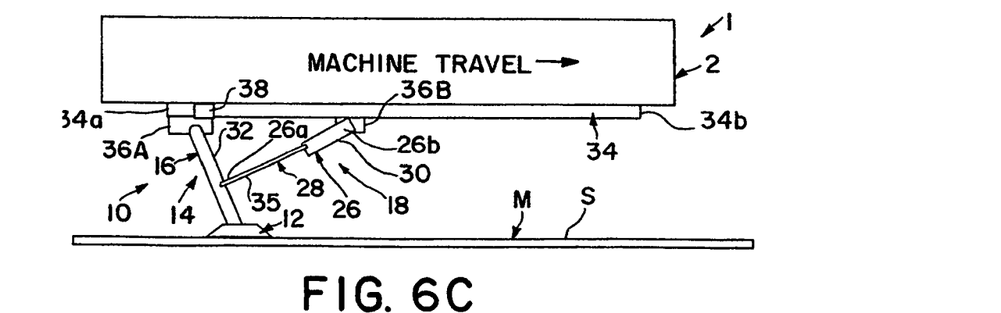
Figure 6D:
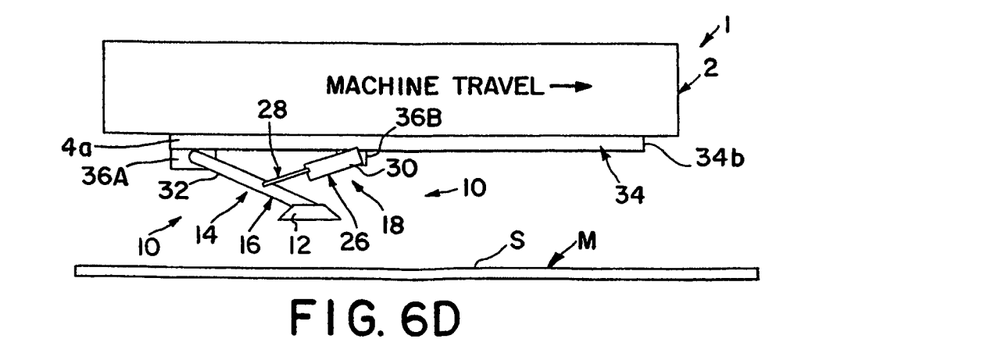

Referring to FIG. 5, the sensor 12 is preferably a density sensor configured to sense density of the material mat M at various locations on the mat upper surface S. Preferably, the sensor 12 is mounted to a generally conical holder device 15 attached to the positioning mechanism 14, as discussed in further detail below. The sensor 12 is configured to generate a signal corresponding to a value of material density of the mat M at any particular position $P_2$ at which the sensor 12 is located. Alternatively, the sensor 12 may be configured to sense a different property of the material mat M, such as for example, temperature, material depth or material thickness. Further, the sensing system 10 may include one or more additional sensors (none shown) for sensing another material property and may include a plurality of each type of sensor, so as to provide for averaging of the sensed property values.

Figure 7:
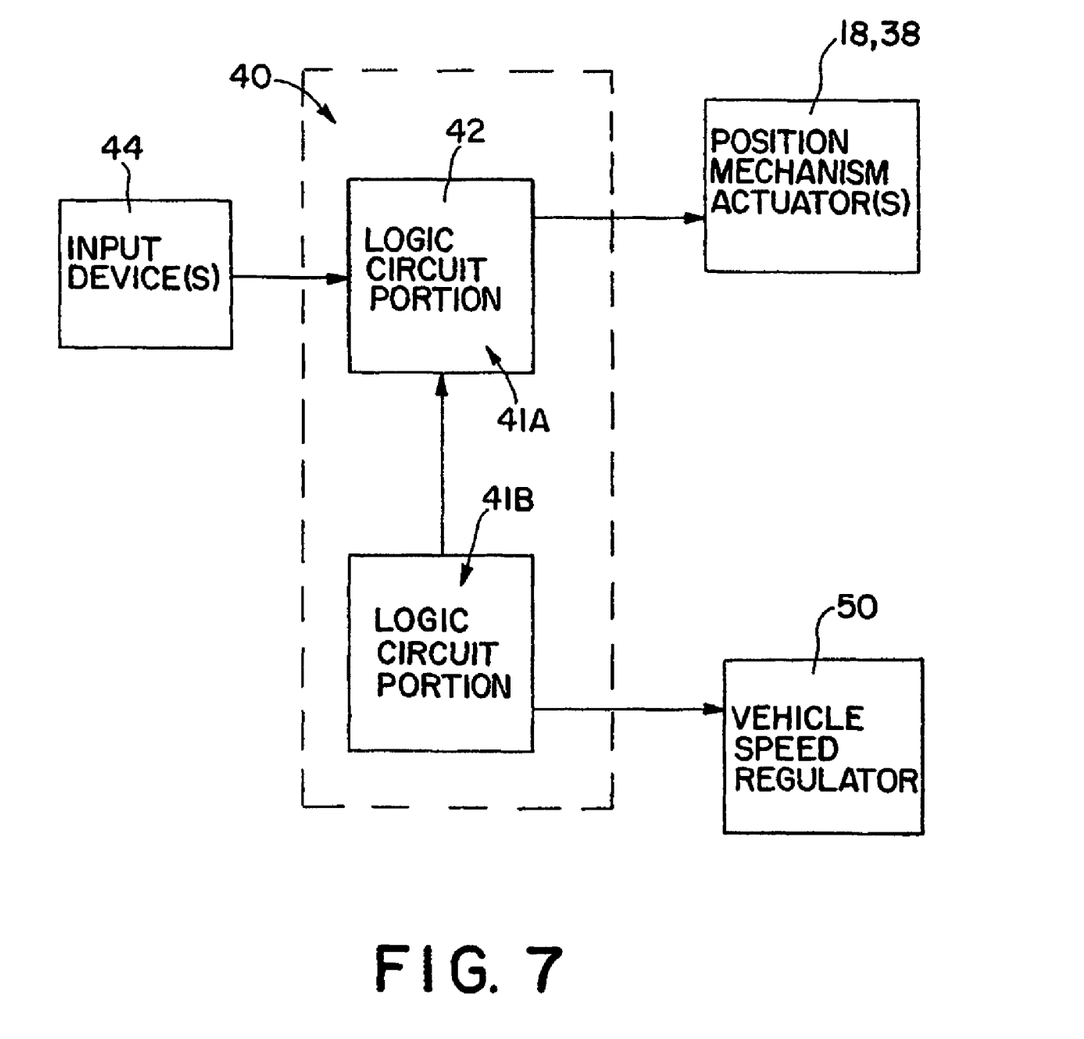
FIG. 7 is a block diagram of a control system used with the sensing system.

Preferably, the sensing system 10 further comprises a display device 46 and a memory or storage device 48, each device 46 and 48 being operatively connected with the sensor 12 and disposed at an appropriate location on the vehicle chassis 2. The sensor 12 is preferably electrically connected with the display device 46 and the storage device 48 through one or more electrical lines 52 extending between the sensor 12 and the devices 46 and 48. The display device 46 is preferably located in the vehicle operator station 4 and is configured to receive density signals from the sensor 12 and to provide a visual indication corresponding to the value of the density at a particular location $P_2$ on the mat M. Preferably, the display device 46 includes an LCD screen 47 configured to display alphanumeric characters corresponding to the values of density sensed by the sensor 12 and is located within the station 4 so as to be viewable by the vehicle operator during a compaction operation. Alternatively, the display device 46 may include any other appropriate type of display, such as an LED screen, and/or may provide a different visual indication, such a graph or scale of density values.

Further, the storage device 48 is configured to receive and store the density signals sent by the sensor 12, such that data corresponding to the density values, and/or other material property values, may be later retrieved to provide a record of properties of the particular material mat M. Preferably, the storage device 48 is a digital electronic memory that stores the values of density as digital records. However, the storage device 48 may be any other appropriate type of storage device, such as for example, a graphic printer device configured to print the value of density at each mat position on a paper record.

Most preferably, the sensor 12, the display device 46 and the storage device 48 are all provided by a modified version of a Pavement Quality Indicator (PQI) Model 300 device commercially available from TransTech Systems Inc. of Schenectady, N.Y. As such, the sensor 12 senses density using an electrical sensing field to sense changes in electrical impedence caused by variances in density of the material mat M from a calibration density. However, the sensor 12, the display device 46 and/or the storage device 48 may be provided by any other commercially available or specially manufactured components and the scope of the present invention is in no manner limited by these devices.

Referring now to FIGS. 1-4 and 6, the positioning mechanism 14 preferably includes an actuator 18 connected with the vehicle 1 and a connective member 16. The connective member 16 has a first end 16a connectable with the sensor 12 and an opposing, second end 16b connected with either the vehicle 1 or the actuator 18. The actuator 18 is configured to displace the connective member first end 16a so as to move the sensor 12 between the first and second sensor positions $P_1$, $P_2$, respectively. Preferably, the connective member first end 16a is attached to an upper surface 15a of the holder device 15, thereby connecting the sensor 12 with the positioning mechanism 14.

Referring to FIGS. 1-4, in a first, preferred construction of the positioning mechanism 14, the actuator 18 is a rotary actuator 22 having a rotatable shaft 23 and the connective member 16 is a flexible connective member 20.

Figure 1A:
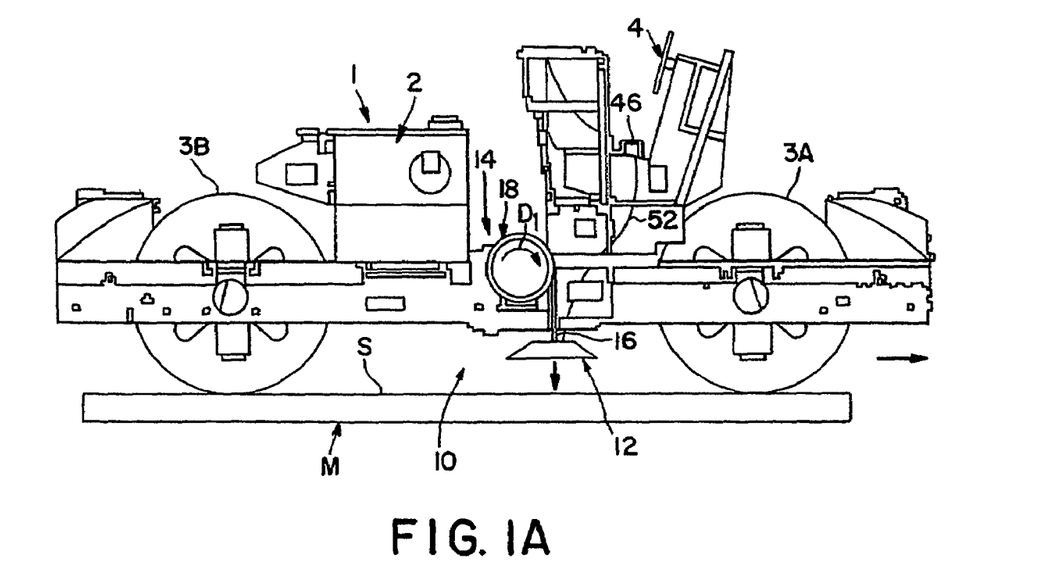
Figure 1B:
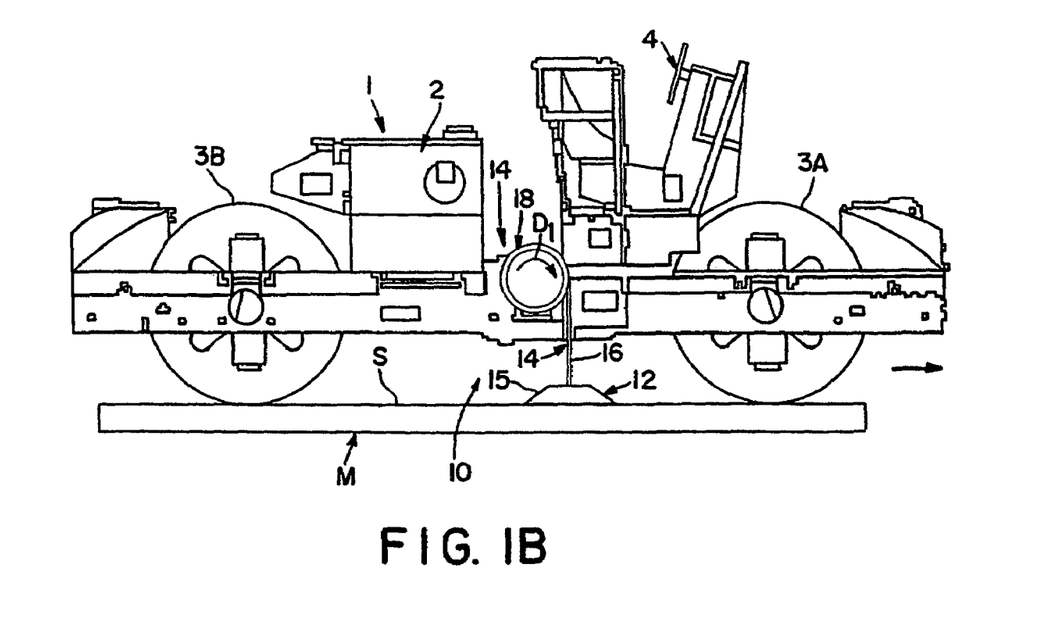
Figure 1C:
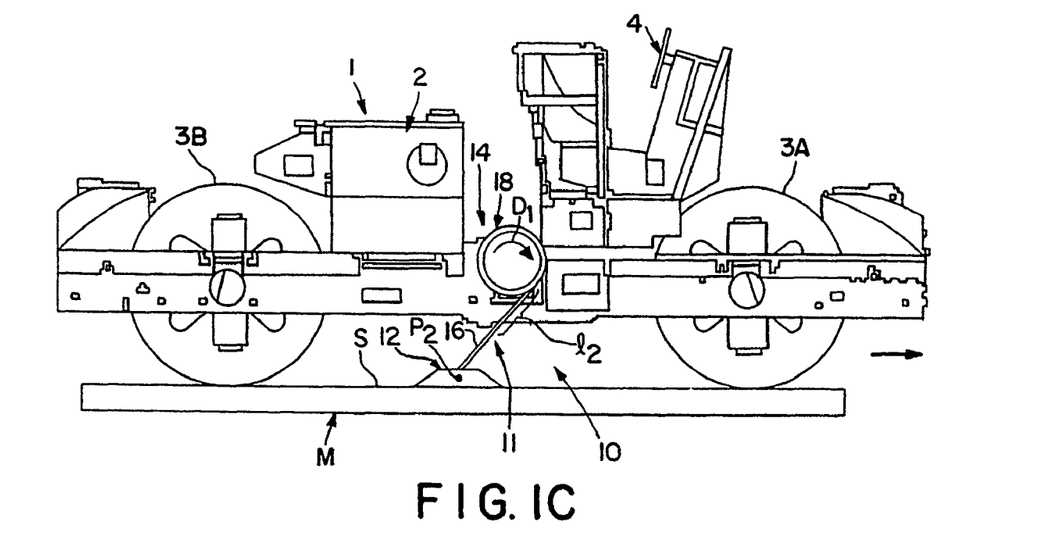
Figure 1D:
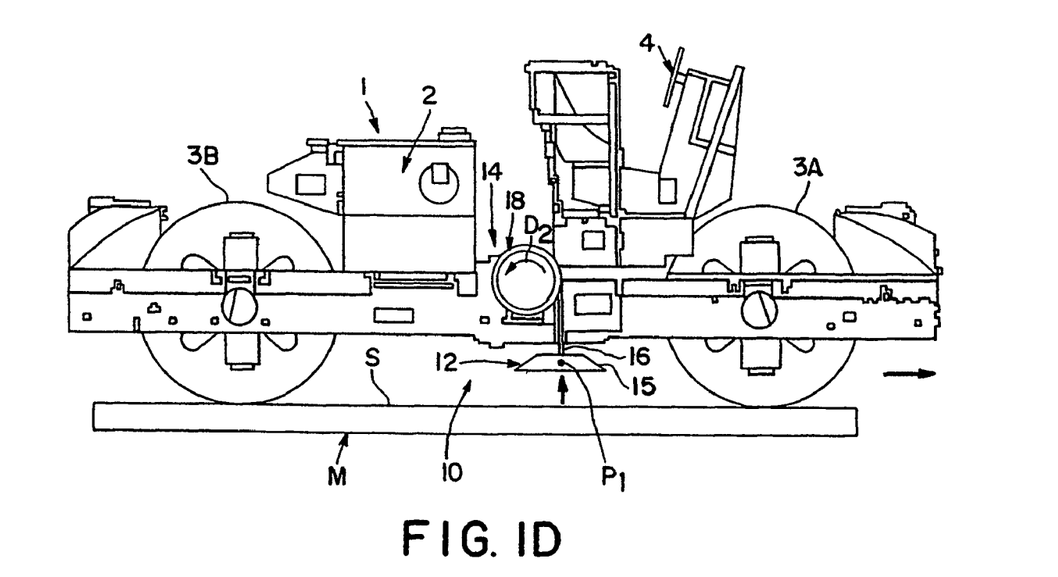
Figure 2:
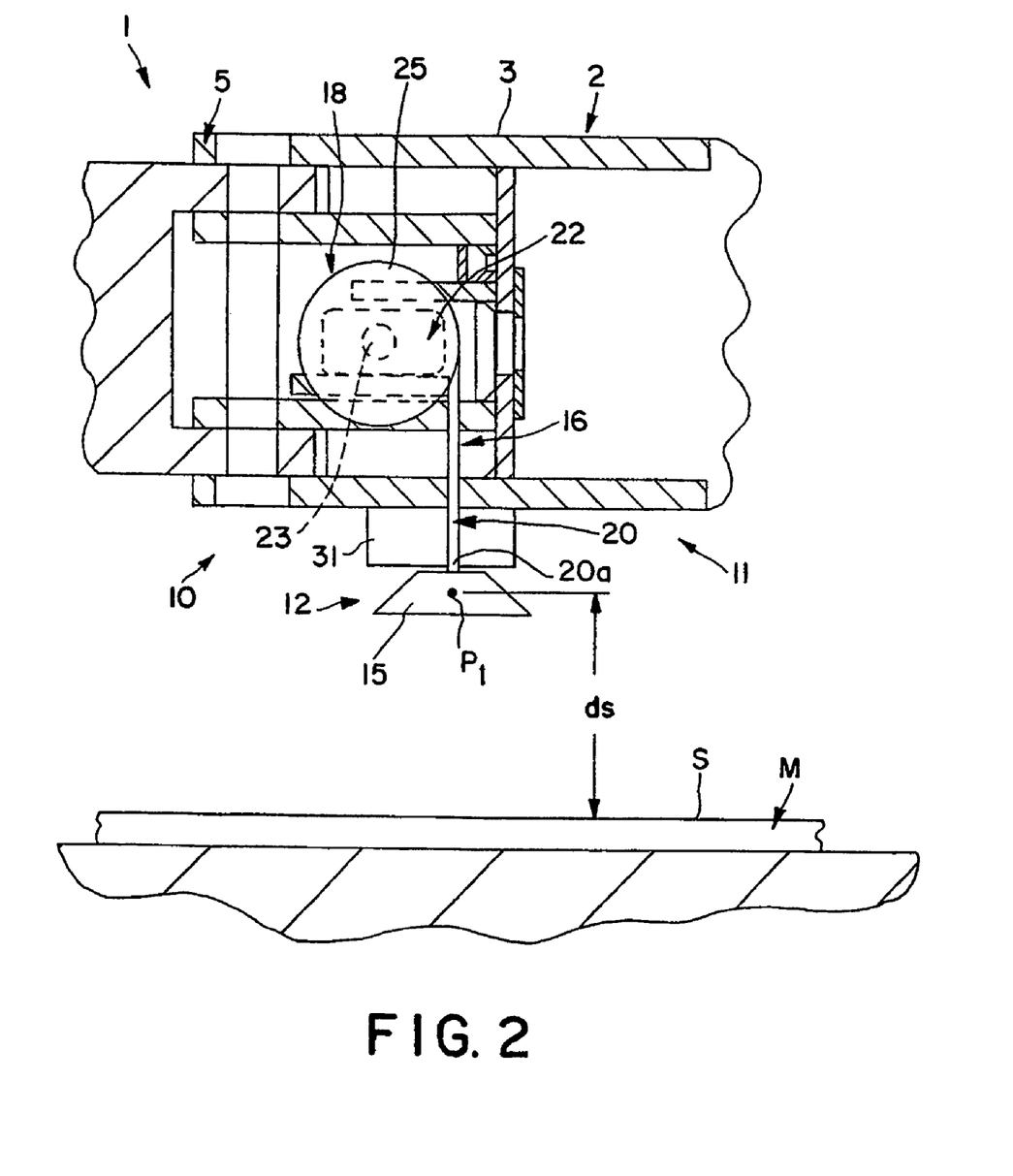
FIG. 2 is an enlarged, broken-away side elevational view of the sensing system depicted in FIG. 1, showing the sensor in a first, upper position.
Figure 3:
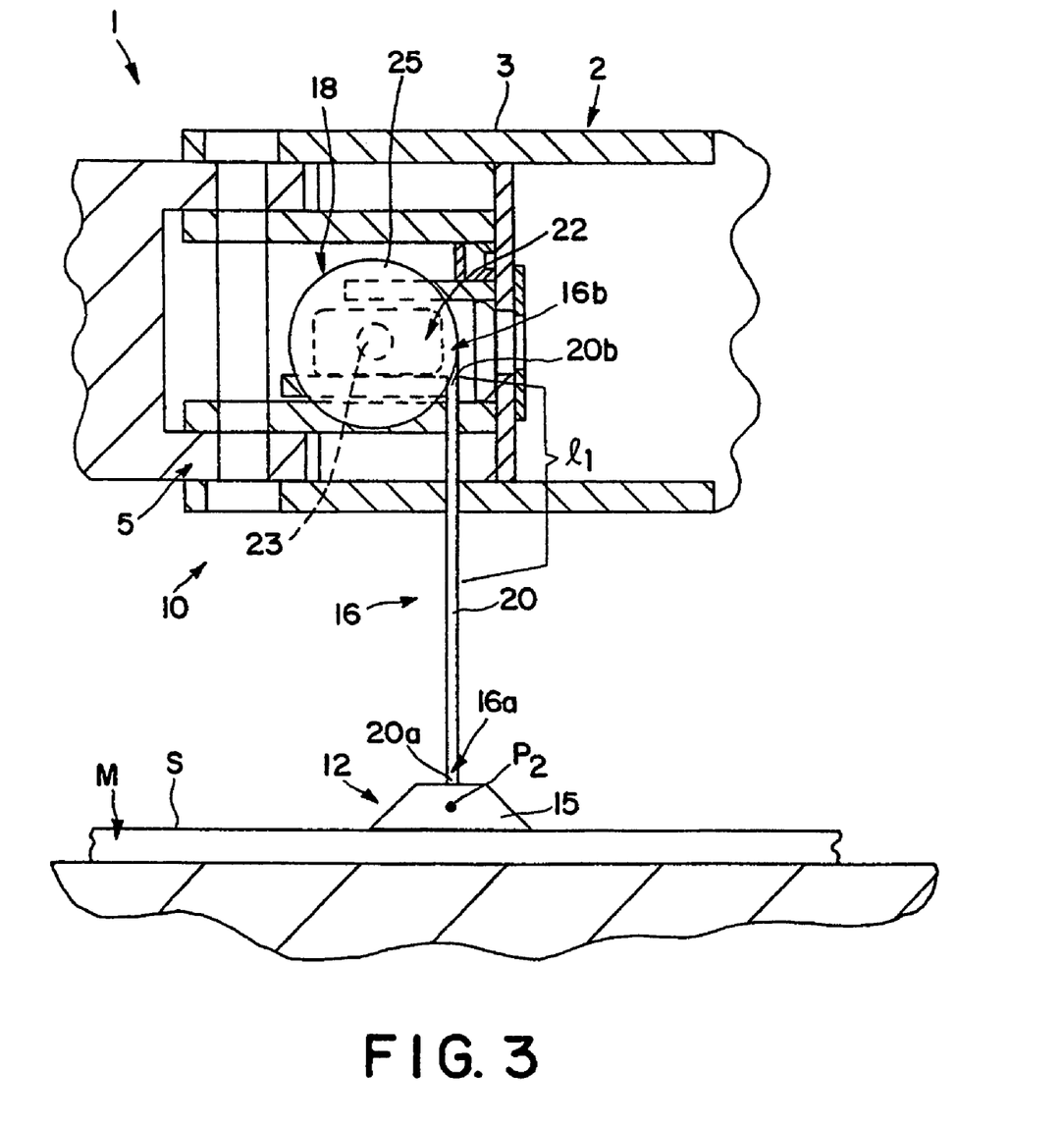
FIG. 3 is another view of the system depicted in FIG. 2, showing the sensor in a second, lower position.
Figure 4:
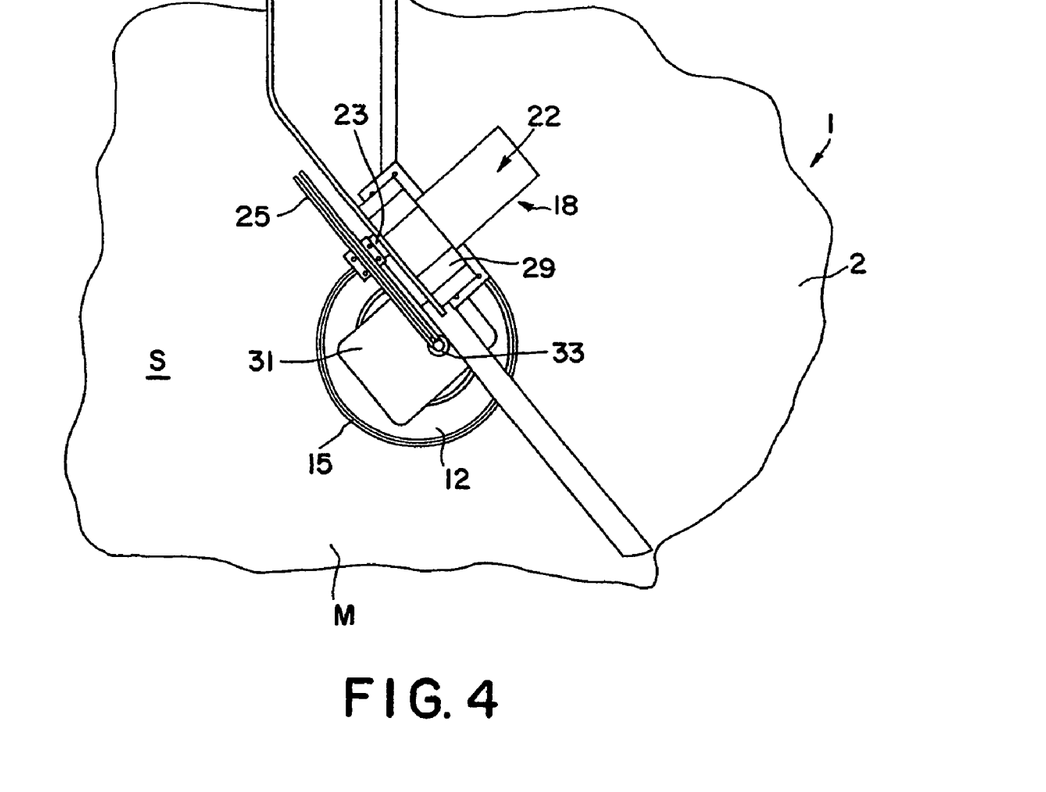
FIG. 4 is a top view of the sensing system depicted in FIG. 2.

The rotary actuator 22 is preferably mounted to the vehicle chassis 2 so as to be located proximal to an articulation joint 5 of an articulated compacting vehicle 1, but may be mounted on any other appropriate location on the chassis 2 or to a separate frame (not shown) connected with the chassis 2. Preferably, as shown in FIG. 4, the rotary actuator 22 includes a reduction gearbox 29 having an output shaft providing the rotatable shaft 23. Alternatively, the actuator 22 may be provided without a gear train or other transmission device, such that the rotatable shaft 23 is the primary shaft of the actuator 22 (FIGS. 2 and 3). Further, the flexible connective member 20 has a second or upper end 20b connected with the actuator shaft 23, most preferably through means of a reel 25, as discussed below. As such, rotation of the shaft 23 in a first direction $D_1$ (FIG. 1A) displaces the sensor 12 from the first position $P_1$ to the second position $P_2$ and rotation of the shaft in a second, opposing direction $D_2$ displaces the sensor 12 from the second position $P_2$ to the first position $P_1$ (FIG. 1D).

Preferably, the first construction of the positioning mechanism 14 further includes a cylindrical reel 25 mounted to the actuator shaft 23, the member second end 21 being attached to the reel 25. The connective member 20 is partially disposed about the reel 25 so as to be alternatively windable upon and unwindable from the reel 25 to displace the sensor 12 between the first and second positions $P_1$, $P_2$, respectively, as discussed in further detail below. Although the reel 25 is preferred, the positioning mechanism 14 may be alternatively constructed without a reel or similar member, such that the flexible connective member 20 is directly attached to and disposed about the actuator shaft 23. Further, the positioning mechanism 14 also preferably includes a support member 31 attached to the vehicle chassis 2 and having a clearance hole 33 (FIG. 4) through which the flexible member 20 extends. When the sensor 12 is located in the first position $P_1$, the upper surface of the sensor holder 15 is disposed generally against the lower surface of the support member 31, such that the lower end 20a of the flexible member 20 (and thus the sensor 12) is generally prevented from moving or swinging with respect to chassis 2 when the sensor 12 is not in use.

Preferably, the flexible connective member 20 is formed as a single wire rope or cable, but may alternatively be provided by one or more chains, belts, hollow flexible tubes or any generally similar flexible mechanical element. Further, the rotary actuator 22 is preferably an electric motor, and most preferably a 12V DC permanent magnet motor Model# 1L473 manufactured by Dayton Motors and available through W.W. Grainger, Inc. Alternatively, the rotary actuator 22 may be a hydraulic or pneumatic motor, an engine or any other appropriate mechanical or electromechanical device capable of producing rotational displacement.

With the above-described first construction, the positioning mechanism 14 functions to displace the sensor between the respective first and second positions $P_1$ and $P_2$ in the following manner. When the logic circuit 40 operates the rotary actuator 22, preferably by control signals as discussed below, the actuator shaft 23 rotates in the first direction $D_1$ to cause a length or portion $l_1$ of the connective member 20 to unwind from the reel 25. As the connective member portion $P_1$ unwinds from the reel 25, gravity causes the sensor 12 to "fall" or displace from the first sensor position $P_1$ until the holder 15 contacts the mat upper surface S, thereby locating the sensor 12 at the second sensor position $P_2$. In order for the preferred density sensor 12 to sense or measure density of the material mat M, the sensor 12 must remain generally stationary at the second position $P_2$ for a period of time sufficient to take a measurement, most preferably for a period of time of between about 1.5 seconds and about 2 seconds. Since the vehicle 1 continues to displace with respect to the material mat M, the actuator 22 continues to rotate the shaft 23 in the first direction $D_1$ in order to cause another portion $l_2$ of the flexible connective member 20 to unwind from the reel 25 (see FIG. 1C). The unwinding of the additional portion or length $l_2$ of the connective member 20 permits the sensor 12 to remain generally disposed in the second position $P_2$ as the vehicle 1 continues to travel upon or adjacent to the mat M. In other words, if the actuator 22 did not unwind the additional portion $l_2$ of the flexible connective member 20, the sensor 12 would be pulled from the second position $P_2$ due to the movement of the vehicle 1.

Thereafter, the actuator 22 rotates the shaft 23 in a second, opposing direction $D_2$ to cause the "unwound" portions $l_2$ and $l_1$ of the connective member 20 to wind back about and become disposed upon the reel 25. Due to the "shortening" of free length of the flexible connective member 20, the holder device 15 is pulled off of the mat upper surface S such that the sensor 12 displaces generally upwardly from the second position $P_2$ toward the first position $P_2$, and thus toward the vehicle chassis 2 (FIG. 1D). When disposed in the first sensor position $P_1$, the sensor 12 spaced a sufficient distance $d_s$ from the mat M so as to generally avoid any potentially damaging contact with the mat M (or with any items located on the mat M).

Referring now to FIG. 6, in a second, alternative construction of the positioning mechanism 14, the actuator 18 is provided by a linear actuator 26 having a first end 26a connected with the connective member 16 and a second end 26b connected with the vehicle 1. The linear actuator 26 is configured such that the actuator first end 26a is displaceable with respect to the actuator second end 26b. Further, the connective member 16 is provided by an elongated link 32 having a first end 32a connected (or connectable) with the sensor 12 and a second end 32b pivotally connected with the vehicle chassis 2. With this mechanism structure, displacement of the actuator first end 26a pivots the link 32 so as to displace the sensor 12 between the first and second sensor positions $P_1$, $P_2$, respectively.

Preferably, the linear actuator 26 is a hydraulic cylinder 28 including a cylinder body 30 and a rod 35. The free end 35a of the rod 35 is connected with the link 32 and the free or outer end 30a of the cylinder 30 is connected with the vehicle 1. With the hydraulic cylinder 28 arranged in this manner, extension of the cylinder rod 28 displaces the sensor 12 from the first position $P_1$ to the second position $P_2$ and retraction of the cylinder rod 28 displaces the sensor 12 from the second position $P_2$ to the first position $P_1$. Although a hydraulic cylinder 28 is preferred, the linear actuator 26 may alternatively be any other appropriate type of linear actuator, such as for example, a pneumatic cylinder, a motor-driven ball screw or a solenoid (none depicted).

Further, the second construction of the positioning mechanism 14 preferably further includes a rail 34 attached to the vehicle 1, preferably to a lower surface 2a of the chassis 2. A first slide member 36A is slidably connected with the rail 34, the link second end 32b being attached to the first slide member 36A. Further, a second slide member 36B is slidably connected with the rail 34 and is spaced apart from the first slide member 36A, the cylinder end 30a being attached to the second slide member 36B. The rail 34 and the sliding members 36A, 36B slidably connect the hydraulic cylinder 28 and the link 32 with the vehicle chassis 2, such that the sensor 12 is able to remain located in the second position $P_2$ for a period of time as the vehicle 1 displaces or travels relative to the material mat M.

More specifically, as the vehicle 1 displaces, the rail 34 moves or slides through the two slide members 36A, 36B, while the cylinder 28 and the link 32 remain in generally fixed positions with respect to the material mat M. When the rear end 34a of the rail 34 reaches the first slide member 36A, the cylinder 28 retracts to displace the sensor 12 from the second position $P_2$ on the mat M to the first vertical position $P_2$ with respect to the mat upper surface S. Further, the second construction of the positioning mechanism 14 preferably includes another or second actuator 38 connected with at least one of the two slide members 36A, 36B. The second actuator 38 is configured to displace the slide members 36, 36B along the rail 34 to the rail front end 34b so as to position the cylinder 28 and link 32, and thus the sensor 12, for use in a subsequent measurement operation. The second actuator 38 may be any appropriate type of-actuator, such as an electric, hydraulic or pneumatic motor, a hydraulic cylinder, etc. and may be mounted on the chassis 2, on one of the slide link halves 36A or 36B, or on a separate frame or member attached to the chassis 2.

Referring now to FIG. 7, the logic circuit 40 is preferably an electric logic circuit electrically connected with the actuator(s) 18 (and 38) of the positioning mechanism 14. The logic circuit 40 is configured to generate and transmit control signals to the actuator(s) 18 (and 38) to operate the mechanism 14 so as to controllably displace the sensor 12 between the first and second sensor positions, in the appropriate manner as described above. Preferably, the logic circuit 40 is an electric logic circuit 40, and most preferably a digital electric circuit, but may alternatively be any other type of logic circuit, such as an analog electric circuit, a hydraulic logic circuit or a pneumatic circuit (none depicted).

Most preferably, the logic circuit 40 includes a first circuit portion 41A connected with the actuator 18 (and actuator 38 in the alternative embodiment) and a second circuit portion 41B operatively connected with a speed regulator 50 of the vehicle 1 and with the first circuit portion 41A. The first circuit portion 41A is preferably a programmable logic controller ("PLC") 42 electrically connected with the rotary actuator 22 or with the linear actuator 26 and the second actuator 38. The first circuit portion 41A is configured to operate the positioning mechanism 14 to displace the sensor between the first and second sensor positions $P_1$ and $P_2$.

The second circuit portion 41B is configured to operate the vehicle speed regulator 50 such that the regulator 50 decreases vehicle speed generally prior to the positioning mechanism 14 displacing the sensor 12 from the first position $P_1$ and to the second position $P_2$, preferably to between about 0.25 and about 0.5 miles per hour (mph). The second circuit portion 41A is also configured to operate the regulator 50 to increase vehicle speed generally after the mechanism 14 displaces the sensor 12 from the second position $P_2$, and thus off of the material mat M. Further, the second circuit portion 41B is configured to initiate operation of the positioning mechanism 14 after the vehicle speed is reduced by sending an appropriate control signal to the first circuit portion 41A. Furthermore, the second circuit portion 41A is also preferably configured to operate the regulator 50 so as to return the vehicle 1 to the speed at which the vehicle 1 was travelling prior to the utilization of the sensing system 10. Preferably, the second circuit portion 41B is a vehicle controller configured to operate various systems of the compacting vehicle 1.

Alternatively, the logic circuit 40 may be constructed with only the first circuit portion 41A, i.e., the PLC 42, and with one or more operator input devices 44 configured to initiate operation of the positioning mechanism 42. More specifically, when the vehicle operator desires to use the sensor device 12, the operator manually reduces vehicle speed and then engages the input device(s) 44 such that the PLC 42 operates the actuator(s) 18 (and 38) such that the positioning mechanism 14 displaces the sensor device 12 through the appropriate set of movements as described above and causes the sensor device 12 to take the desired material property measurements. As yet another alternative, the sensing system 10 may be constructed without any logic circuit or controller, such that the vehicle operator directly operates the actuator(s) 18 of the positioning mechanism 14.

It will be appreciated by those skilled in the art that changes could be made to the embodiments or constructions described above without departing from the broad inventive concept thereof. It is understood, therefore, that this invention is not limited to the particular embodiments or constructions disclosed, but it is intended to cover modifications within the spirit and scope of the present invention as generally described herein.

What is claimed is:

1. A device for deploying a sensor from a moving construction vehicle, the sensor being used to sense a property of a material mat having an upper surface, the deployment device comprising:

a positioning mechanism connected with the vehicle and connectable with the sensor, the mechanism being configured to displace the sensor between first and second vertical positions with respect to the material mat as the vehicle displaces with respect to the mat, the first sensor position being spaced a substantial distance above the mat upper surface and the second sensor position being located one of proximal to the mat surface and on the mat surface, the sensor being able to sense the material property when disposed in the second position, the positioning mechanism including a flexible connective member having a first end connectable with the sensor and an opposing second end and a rotary actuator connected with the vehicle and having a rotatable shaft, the member second end being connected with the shaft such that rotation of the shaft displaces the sensor between the first and second sensor positions.

2. The deployment device as recited in claim 1 further comprising a logic circuit configured to operate the positioning mechanism such that the mechanism sequentially displaces the sensor from the first position to the second position, permits the sensor to remain generally disposed at the second position for a period of time, and displaces the sensor from the second position to the first position after lapse of the period of time.

3. The deployment device as recited in claim 2 wherein the logic circuit is a operatively connected with the actuator and configured to operate the actuator so as to controllably displace the sensor.

4. The deployment device as recited in claim 2 wherein:
the vehicle includes a speed regulator configured to adjust vehicle travel speed; and
the logic circuit is operatively connected with the speed regulator and is further configured to operate the regulator such that the regulator decreases vehicle speed generally prior to the positioning mechanism displacing the sensor from the first position to the second position and increases vehicle speed generally after the mechanism displaces the sensor from the second position.

5. The deployment device as recited in claim 1 wherein the positioning mechanism further includes a reel mounted to the actuator shaft, the flexible connective member second end being attached to the reel such that the connective member is partially disposed about the reel and rotation of the actuator shaft in a first direction causes a portion of the connective member to unwind from the reel so as to displace the sensor from the first position to the second position and rotation of the actuator shaft in a second, opposing direction causes the portion of the connective member to wind about the reel so as to displace the sensor from the second position.

6. The deployment device as recited in claim 5 wherein when the sensor is disposed in the second position, further rotation of the actuator shaft in the first direction causes another portion of the flexible connective actuator to unwind from the reel such that the sensor remains generally disposed in the second position as the vehicle displaces with respect to the material mat.

7. A device for deploying a sensor from a construction vehicle, the sensor being used to sense a property of a material mat having an upper surface, the deployment device comprising:
a flexible connective member having a first end connectable with the sensor and an opposing second end; and
a rotary actuator connected with the vehicle and having a rotatable shaft, the connective member second end being connected with the shaft such that rotation of the shaft displaces the sensor between a first position spaced a substantial distance above the mat upper surface and second position located one of proximal to the mat surface and on the mat surface, the sensor being able to sense the material property when disposed in the second position.

8. The deployment device as recited in claim 7 further comprising a logic circuit configured to operate the rotary actuator such that the actuator sequentially displaces the sensor from the first position to the second position, permits the sensor to remain generally disposed at the second position for a period of time, and displaces the sensor from the second position to the first position after lapse of the period of time.

* * * * *